United States Patent [19]

Quakenbush

[11] Patent Number: 5,099,080
[45] Date of Patent: Mar. 24, 1992

[54] PROCESS FOR PREPARING DINITROTOLUENE

[75] Inventor: Allen B. Quakenbush, Lake Charles, La.

[73] Assignee: Olin Corporation, Cheshire, Conn.

[21] Appl. No.: 666,330

[22] Filed: Mar. 8, 1991

[51] Int. Cl.$^5$ ............................................ C07C 205/06
[52] U.S. Cl. ................................... 568/934; 568/939; 568/940
[58] Field of Search .................... 568/934, 939, 940

[56] References Cited

U.S. PATENT DOCUMENTS

| | | | |
|---|---|---|---|
| 3,928,395 | 12/1975 | Seha et al. | 568/939 X |
| 3,957,889 | 5/1976 | Milligan et al. | 568/939 X |
| 4,064,147 | 12/1977 | Thelen et al. | 568/939 X |
| 4,804,792 | 2/1989 | Mason et al. | 568/939 |
| 4,918,250 | 4/1990 | Mason et al. | 568/934 |
| 5,001,272 | 3/1991 | Mason | 568/934 |

Primary Examiner—Robert L. Stoll
Assistant Examiner—Chhaya Sayala
Attorney, Agent, or Firm—Dale Lynn Carlson

[57] ABSTRACT

Described herein is a one pot continuous improved process for preparing dinitrotoluene by reacting toluene with concentrated nitric acid.

2 Claims, No Drawings

PROCESS FOR PREPARING DINITROTOLUENE

FILED OF THE INVENTION

This invention relates to an improved continuous process for preparing dinitrotoluene by reacting nitric acid with toluene. The improved process utilizes the circulating stream of reactor liquor to provide a heat sink for the fast and highly exothermic nitration reaction.

BACKGROUND OF THE INVENTION

Nitration reactions of aromatic hydrocarbons are generally conducted in mixed acid systems, such as mixed nitric and sulfuric acids. However, these mixed acid systems usually involve reconcentration of the spent sulfuric acid after the nitration reaction. This reconcentration step is time consuming, energy intensive and requires the use of expensive materials of construction. In addition, the use of sulfuric acid tends to result in significant nitrocreosol and cyanide by-product formation which requires expensive wastewater treatment to remove.

In view of these disadvantages associated with mixed nitric/sulfuric acid systems, there have been recent attempts to perform gas phase or liquid phase nitrations in concentrated nitric acid in the absence of sulfuric acid. By way of illustration:

U.S. Pat. No. 3,928,395 describes a process for nitrating unsubstituted or substituted benzene at a reaction temperature of −40° C. to 80° C. using 90% to 100% nitric acid in the optional and preferred presence of a dipolar aprotic solvent, wherein the reaction is halted by means of a dipolar aprotic solvent.

U.S. Pat. No. 3,957,889 describes an improved process for nitrating toluene or ortho-xylene with nitric acid, the improvement being enhancing the rate of the nitration reaction by carrying it out in the presence of at least an effective amount of anhydrous calcium sulfate or soluble anhydrite.

U.S. Pat. No. 4,064,147 describes the preparation of aromatic mononitro compounds (such as mononitrobenzene) by a liquid phase reaction with nitric acid having an acid concentration of between 70% and 100% by weight using a reaction temperature of between 0° C. and 80° C. When employing a relatively reactive compound such as benzene or toluene as a starting material, this patent teaches that a nitric acid concentration of between 70 and 90% by weight is preferred. The process of this patent requires a ratio of nitric acid plus water to organic components of not below 3 when using 70% nitric acid, and not below 8 when using 100% nitric acid. However, it has now been found that such a high acid ratio using 100% nitric acid tends to favor dinitro-compound production, not desired by the process of the patent.

U.S. Pat. No. 4,804,792 describes the nitration of benzene and toluene by contacting these with concentrated nitric acid in the presence of a molten nitrate salt. The patent states that the molten salt serves as a temperature regulator for the reaction and as an isothermal medium for the reactants. A preferred method of contacting the reactants in the presence of the molten salt is stated to be by bubbling the reactants into a bath of the molten salt by means of a carrier gas such as nitrogen. The vapor phase reaction is stated to be carried out at a temperature of between 150° C. and 250° C.

U.S. Pat. No. 4,918,250 describes a process for nitrating toluene to dinitrotoluene (DNT) and phase separation of the product using an inorganic salt as a phase separation agent. In this patent, DNT is produced in a two-step liquid phase nitration reaction between nitric acid and toluene in the absence of sulfuric acid and solvent. In the process of the patent, the inorganic salt is incorporated into the mixture of DNT and unreacted nitric acid in an amount sufficient to cause phase separation of the mixture in order to facilitate isolation of the DNT from the unreacted nitric acid in the product mixture (col. 2, lines 27-33).

Nitration of aromatics proceeds at different rates depending on temperature, acid concentration, mixing conditions, and reactant ratios. At a given condition, nitration rate decreases as more nitrate groups are substituted onto the aromatic ring. The first nitrate groups attached to the ring are added the fastest. Nitration of toluene to o-nitrotoluene releases about 25,300 kcal/mole. The heat of reaction to form p-nitrotoluene is 33,700 kcal/mole. Batch experiments have attempted to measure the reaction rate at 0° C. and a 9 to 1 feed molar ratio of acid to toluene. The mononitration is completed in seconds before a proper sample can be taken. At proposed optimum reaction conditions of 50° C., the reaction would be almost instantaneous. The mononitration would occur almost at the speed the toluene and acid are mixed, i.e., mass transfer controlled instead of kinetically controlled. At these kinetic rates, undesirable local hot spots can develop if the toluene is not mixed properly with the acid. These hot spots cause the nitric acid to form nitrogen oxides which cause nitric acid loss and promote organic by-product formation. Thus, there is a need to essentially eliminate the formation of these hot spots.

DESCRIPTION OF THE INVENTION

The instant improved process produces dinitrotoluene from toluene and concentrated nitric acid in a one pot continuous process. The improvement of the instant process comprises injecting toluene into a volumetrically larger circulating stream. The circulating stream of reactor liquor provides a heat sink for the fast and highly exothermic nitration reaction. The improved process reduces local hot spots at the point where the toluene is injected into the nitric acid. This process reduces the local temperature excursions and reduces the overall acid losses and organic by-product formation.

In the practice of the process of this invention, a continuous stirred tank reactor liquor is pumped at high rates in a conduit. The feed aromatic is injected into the circulating reactor media. The reaction media is a homogeneous mixture containing nitric acid, water, and the nitrated aromatics. The flow ratios of the circulation stream to the injected aromatic are determined by the heat of reaction and specific heats of the streams. By injecting 1 volume of toluene into 100 volumes of circulating reaction media, the temperature rise is limited to 5° C. If the ratio is reduced to 1 to 50, a 10° C. rise is measured in the mixed stream.

The dinitrotoluene may then be further purified to the desired specifications. The one pot continuous process of this invention provides an efficient method for preparing dinitrotoluene.

In the process of this invention, toluene is reacted with concentrated nitric acid (an acid concentration of between 95 and 100 weight percent, preferably at least 98 weight percent) at a temperature from about 0° C. to about 90° C., preferably from about 40° C. to about 70° C. to produce an effluent mixture of dinitrotoluene, water and unreacted nitric acid.

The molar ratio of toluene to nitric acid employed in the reaction is generally between about 20:1 and 7:1, preferably from 12:1 to 9:1. The reaction is generally conducted at atmospheric pressure, although a higher pressure can be employed, if desired. The reaction time is typically less than about 4 hours, preferably less than about 40 minutes.

The effluent mixture of dinitrotoluene, water and unreacted nitric acid can then be mixed with an inorganic nitrate salt. The addition of nitrate salt allows DNT to be separated from the mixture by decanting. The salts which may be used to cause phase separation include a wide variety of nitrate salts which may be in various hydrated states.

While the invention has been described above with reference to specific embodiments thereof, it is apparent that many changes, modifications, and variations can be made without departing from the inventive concept disclosed herein. Accordingly, it is intended to embrace all such changes, modifications, and variations that falls within the spirit and broad scope of the appended claims. All, patents cited herein are incorporated by reference in their entirety.

What is claimed is:

1. A continuous improved one pot process for the production of dinitrotoluene by a nitration reaction which comprises injecting toluene into a circulating reactor liquor consisting essentially of nitric acid and water, said reactor liquor providing a heat sink for the nitration reaction, said nitration reaction being conducted at a temperature of between about 0° C. and about 90° C. employing a molar ratio of nitric acid to toluene of between 12:1 and 9:1, said toluene being injected into said reactor liquor in a volume ratio of between 1:100 and 1:50 based upon the volume of said reaction liquor.

2. The process of claim 1 which is carried out at a reaction temperature of between about 40° C. and about 70° C. to produce an effluent mixture of dinitrotoluene, water and unreacted nitric acid, and wherein said effluent mixture is mixed with a nitrate salt to cause phase separation of the dinitrotoluene from the effluent mixture.

* * * * *